(12) United States Patent
Litovitz

(10) Patent No.: US 6,263,878 B1
(45) Date of Patent: Jul. 24, 2001

(54) MEANS FOR PROTECTING LIVING SYSTEMS FROM ADVERSE EFFECTS OF ELECTRIC, MAGNETIC AND ELECTROMAGNETIC FIELDS

(75) Inventor: Theodore A. Litovitz, Annapolis, MD (US)

(73) Assignee: The Catholic University of America, Washington, DC (US)

( * ) Notice: Subject to any disclaimer, the term of this patent is extended or adjusted under 35 U.S.C. 154(b) by 0 days.

(21) Appl. No.: 07/642,417

(22) Filed: Jan. 17, 1991

(51) Int. Cl.$^7$ .................................................. A61B 19/00
(52) U.S. Cl. .............................................. 128/897; 600/9
(58) Field of Search ..................... 600/9–15; 128/897–98

*Primary Examiner*—John P. Lacyk
(74) *Attorney, Agent, or Firm*—Pillsbury Winthrop LLP

(57) ABSTRACT

An arrangement for inhibiting the adverse effect of an ambient time varying field having an electric component of 5 Kv/M or less and/or a magnetic component of 500 $\mu$T or less on a living system. To provide protection, at least one of the characteristic parameters of said field to which the living system is exposed is changed within time intervals of less than 10 seconds.

80 Claims, 2 Drawing Sheets

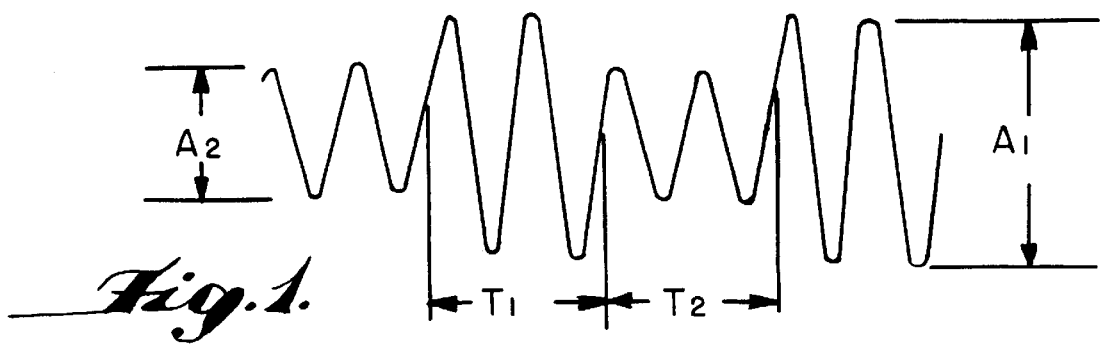
Fig.1.
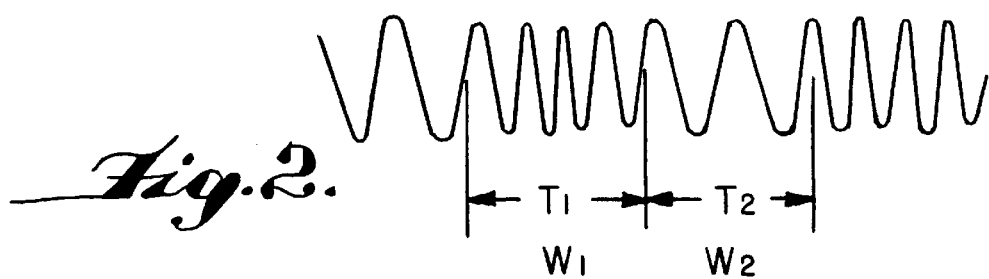
Fig.2.
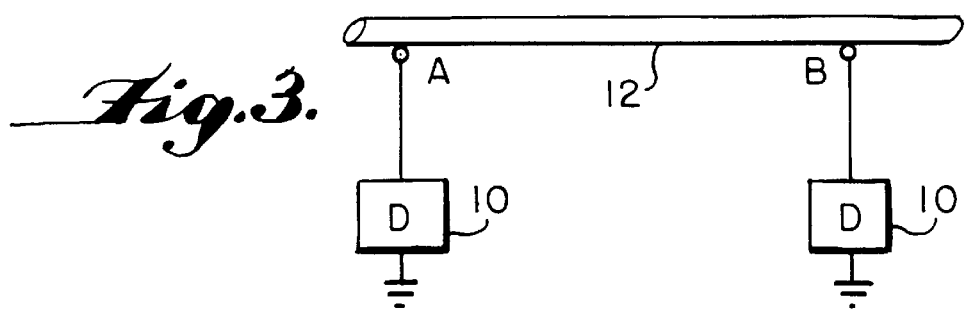
Fig.3.
Fig.4.
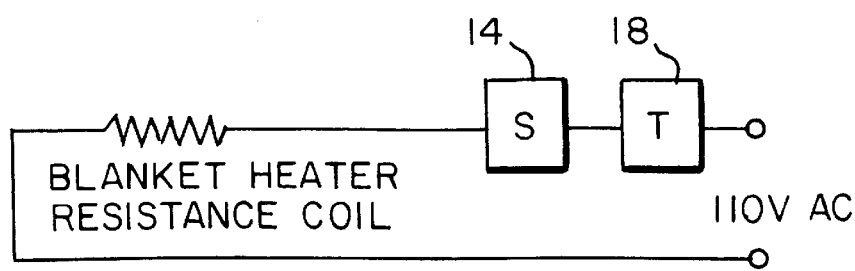

MEANS FOR PROTECTING LIVING SYSTEMS FROM ADVERSE EFFECTS OF ELECTRIC, MAGNETIC AND ELECTROMAGNETIC FIELDS

BACKGROUND OF THE INVENTION

1. Field of the Invention

This invention relates to methods and apparatus for protecting living systems from adverse effects upon them of electric fields, magnetic fields and electromagnetic fields.

2. Background and Discussion of Related Art

For some years past there has been a growing recognition and concern that humans are suffering adverse effects, notably cancers, from living and/or working in ambient electromagnetic fields, particularly those fields which are alternating or pulsating or being modulated at frequencies below 500 Hz. Ambient frequencies particularly identified with an enhanced risk of cancer are those "power" frequencies at 60 Hz (U.S.) and 50 Hz (U.K. and continental countries). Electromagnetic fields existing near devices using cathode ray tubes also are implicated, due to fields generated by the magnetic electron beam deflecting devices included in the tube control apparatus.

Various articles have been published on the electromagnetic field problem. Over the past 11 years a series of epidemiological studies have found that low level electromagnetic fields [even as low as 1 $\mu$T (1 micro Tesla) for 60 Hz power line fields] can be correlated with increased incidence of certain diseases. This correlation is strongest for those who have lived or worked in this environment for many years. For example, an increased risk of cancer has been found among children who lived for several years close to power lines (Wertheimer, N. and Leeper, E. "Electrical Wiring Configurations and Childhood Cancer", AM. J. EPIDEMIOLOGY, 109. 273–284 (1979); also, Savitz, D. A. et al., "Case Control Study of Childhood Cancer and Exposure to 60-Hertz Magnetic Fields," AM. J. EPIDEMIOLOGY, 128, 10–20 (1988); also, Milham, S. Jr., "Increased Mortality in Amateur Radio Operators Due to Lymphatic and Hematopoietic Malignancies," AM. J. EPIDEMIOLOGY, 128, 1175–1176 (1988). The research indicates that children from high electromagnetic field exposure homes have a 50 percent greater risk of developing cancer, particularly leukemia, lymphomas, and nervous system tumors. Other data also show that men working in electrical jobs, such as electricians and telephone lineman are at higher risk for brain tumors and other cancers. In a recent study in the Los Angeles area, S. Preston-Martin and collaborators at the University of Southern California found that men who had worked for 10 years or more in a variety of electrical occupations had a ten times greater chance of getting brain tumors than men in the control group. [Preston-Martin, S., and Mack, W. and Peters, Jr. "Astrocytoma Risk Related to Job Exposure to Electric and Magnetic Fields," presented at DOE contractors Annual Review, Denver Colo., Nov. 5–8, 1990.] A study performed by G. Matanoski of Johns Hopkins University found a dose response relationship for cancers in male New York Telephone employees from 1976 to 1980. [Matanoski, G., Elliot, E. and Breysse, P. Poster presented at the annual DOE/EPRI Contractors Review of Biological Effects from Electric and Magnetic Fields, November 1989, Portland, Oreg.] Matanoski measured the average magnetic field exposure among different types of employees and then installation and repair workers. A comparison of the cancer rates among the various types of employees showed that cable splicers were nearly twice as likely to develop cancer as those employees who did not work on telephone lines. Among central office workers those who were exposed to the short intense fields of telephone switching equipment the rates of occurrence of cancers were unusually high, although not as high as for cable splicers. The central office workers were more than three times as likely to get prostate cancer and more than twice as likely to get oral cancer as co-workers who were less exposed. And there were two cases of male breast cancer, a disease so rare that no cases at all would be expected.

The 60 Hz electromagnetic fields found in residential settings can vary from about 0.05 $\mu$T to over 1000 $\mu$T. In-vitro experiments have definitely shown that changes in biological cell function can occur in fields as low or lower than 1 $\mu$T and as high as 500 $\mu$T. R. Goodman and collaborators [Goodman, R. and Henderson, A., "Sine Waves Enhance Cellular Transcription, "BIOELECTROMAGNETICS, 7, 23–29, 1986)] have shown that RNA levels can be increased by electromagnetic fields ranging in frequency from 15 to 4400 Hz with amplitudes of 18 to 1150 $\mu$T. They have shown that the RNA levels can be enhanced by factors of ten or more. Jutilainen and coworkers [Jutilainen, J., Laara, E. and Saali, K., INT. J. RADIAT. BIOL.,52, 787–793, (1987)] have shown that 1 $\mu$T 50-Hertz electromagnetic fields can induce abnormalities in chick embryos. Thus, electromagnetic fields appear not only to be carcinogenic, but also capable of inducing birth defects. Pollack and collaborators, C. T. Brighton, E. O'Keefe, S. R. Pollack and C. C. Clark, J. ORTH. RES. (to be published), have shown that electric fields as low as 0.1 mv/cm at 60 kHz can stimulate growth of bone osteoblasts. McLeod and collaborators have found that in the region between 1 Hz and 100 Hz, much lower fields are needed to stimulate fibroblast growth than at frequencies above and below this range [McLeod, K. J., Lee, R. and Ehrlich, H., "Frequency Dependence of Electric Field Modulation of Fibroblast Protein Synthesis," SCIENCE, 250, 1465 (1987)].

Reported related research on animals is not as extensive as for humans, but there is every reason to believe that the same adverse effects occur in them as in humans. Therefore, protection of living systems including but not limited to humans and animals are encompassed within the present invention.

SUMMARY OF THE INVENTION

I have concluded that the aforesaid adverse health effects upon living systems (including but not limited to single cells, tissues, animals and humans) may be inhibited by changing in time one or more of the characteristic parameters of the ambient time varying electric, magnetic or electromagnetic field to which the living system is exposed. This may be done in a number of ways, for example, by changes in one or more of frequency (period), amplitude, phase, direction in space and waveform of the field to which the living system is exposed. As for the time periods between changes, I have concluded that these time periods should be less than approximately ten (10) seconds, and preferably should not exceed approximately one (1) second. The changes may occur at regular or irregular intervals. These changes can be accomplished by superimposing these special time-dependent fields upon the ambient field, or by changing with time the characteristic parameters of the original fields.

The change or changes in the ambient field should be about 10 percent or more of the related characteristic parameters of the field before the change.

My proposal to protect living systems from the adverse effects of electric, magnetic or electromagnetic fields by creating special ambient fields as aforesaid is based on my conclusion that something must be done to confuse the biologic cell so that it can no longer respond to the usual fields found in the home and work place. I have discovered that the fluctuating fields mentioned above will prevent the adverse effects of the usual environmental fields. As above stated, these fluctuations can occur either in the amplitude, frequency (period), phase, wave form or direction-in-space of the newly created "confusion" field.

To affect cell function some insult (e.g. drug, chemical, virus, electromagnetic field, etc.) will cause a signal to be sent from receptors (often at the cell membrane) into the biochemical pathways of the cell. Although the exact receptor and signaling mechanism utilized by the cell to recognize the fields is not known, I have discovered that this mechanism can be stopped by confusing the cell with fields that vary in time in the ways specified herein.

For example, a 60 Hz electromagnetic field having a magnetic component of 10 $\mu$T can cause a two fold enhancement of the enzyme ornithine decarboxylase. If this field is abruptly changed in frequency, amplitude, wave form, direction or phase at intervals of more than 10 seconds, the two fold enhancement persists. If, however, the frequency, amplitude or waveform parameters are changed at approximately 1 second intervals, the electromagnetic field has no effect. The cell does not respond because it has become confused. Similar electric fields in tissue with amplitudes ranging from 0.1 to 50 $\mu$v/cm. can be useful in protecting the living system from adverse effects. To create these fields at 60 Hz. the field strength outside the living systems must be about one million times larger (i.e. 0.1 to 50 v/cm.)

I consider that my invention functions with ambient fields having an electric component of 5 Kv/M or less and/or a magnetic component of 500 $\mu$T or less. As for lesser field strengths, electric components of 0.5 Kv/M and/or magnetic components of 50 $\mu$T are exemplary.

For best results the confusion field should contain frequency components similar to that contained in the ambient fields. The vector component of the "confusion" field along the direction of the ambient field should be approximately the same as the value of the ambient field. The time between changes in properties such as frequency, phase, direction, waveform or amplitude should be less than 5 seconds for partial prevention of adverse effects but preferably less than 1 second for much more complete protection.

It is preferred to have the field to which the living system is exposed be my confusion field for the duration of the exposure. However, benefit will be achieved if my confusion field is in existence for only a major portion of the total exposure time.

I have referred above to electric, magnetic and electromagnetic fields because, insofar as they are distinct, ambient fields of each type are capable of causing harm to living systems, but if changed according to my invention will inhibit the on-set of adverse effects. For convenience in the remainder of this specification and in the claims, I use the term electromagnetic field as a generic description embracing the three types of fields.

DISCUSSION OF BACKGROUND OF THE INVENTION

To the best of my knowledge, to date no one has heretofore proposed my invention, although over ten years have elapsed since the first recognition of the dangers of chronic electromagnetic field exposures to humans.

There have been many teachings about the use of electromagnetic fields to treat humans for pre-existing diseases or conditions. For example, U.S. Pat. No. 4,066,065 (Kraus 1978) describes a coil structure to create a magnetic field for treatment of a hip joint. U.S. Pat. No. 4,105,017 (Ryaby 1978) describes a surgically non-invasive method of and apparatus for altering the growth, repair or maintenance behavior of living tissues by inducing voltages and concomitant current pulses. U.K. Patent GB 2 188 238 A (Nenov et al. 1986) describes an apparatus alleged to provide analgesic, trophic and anti-inflammatory effects. Costa (1987) U.S. Pat. 4,665,898 describes a magnetic coil apparatus for treatment of malignant cells with little damage to normal tissue. An apparatus for treatment of diseases of the peripheral and autonomic nervous system as well as other diseases has been described by Solovleva et al. ("Polyus-1' Apparatus for Low-Frequency Magnetotherapy," G. Soloreva, V. Eremin and R. Gorzon, BIOMEDICAL ENGINEERING (Trans. of: Med. Tekh, (USSR)), Vol. 7, No. 5, pp. 291–4 (1973).

The above procedures are usually referred to as "magnetotherapeutic" procedures. My invention focuses instead on the prevention of disease caused by long term exposure to ambient time varying electromagnetic fields. To date, no other proposals have been presented which utilize modifications of the time dependence of the ambient fields to prevent adverse health effects of ambient electromagnetic fields. Basic to all the patents and articles which describe the treatment of pre-existing diseases by electromagnetic fields (magnetic therapy) is the assumption that electric or magnetic fields (often of large magnitude, e.g. 1 to 100 T Ryaby 1978), if applied for some limited period of time, can beneficially alter the functioning of the cells and tissues within living systems. Now that it is known that chronic, long term exposure to even very low level, time varying electromagnetic fields (e.g., magnetic fields as low as 0.5 $\mu$T) can cause some of the very diseases which short term therapeutic doses of these fields are used to treat. Methods of protection from the biological effects of magnetic fields have been sorely needed. To find this protection it was necessary for me to recognize that magnetic therapy is carried out by affecting biologic cell function. It had to be realized that if magnetic therapy does not affect the physiological functioning of the living system then no therapeutic effect could result. What was needed, which the present invention provides, is a method of modifying the ambient fields in which living systems exist in such a way that they have no effect on cell function. This modified field has no utility in the treatment of any disease or biologic malfunction. This modified field is not of any use in magnetic therapy. However, this modified field (because it does not affect the function of the cells and tissues of the living system) has no adverse health effects. Thus, long term exposure to these modified fields will be safe. These modified fields would not, for example, increase the risk of developing cancer.

However, none of the above authors, or anyone else before me, had discovered that periodically changing these very low ambient fields as described elsewhere herein can prevent harmful effects of electromagnetic fields.

OBSERVATIONS IN SUPPORT OF THE INVENTION

I have been able to support the operability of my invention by several observations and procedures. One observation has been the effect of coherence time (defined herein as the time interval between changes of the characteristic parameters of the fields) of the applied field on bioelectromagnetic enhancement of ornithine decarboxylase (ODC) specific activity.

Specific activities of this highly inducible enzyme were examined following mammalian cell culture exposure to electromagnetic fields. Monolayer cultures of logarithmically growing L929 cells were exposed to fields alternating between 55 and 65 Hz. The magnetic field strength was 1 µT peak. The cells were exposed to the fields for four hours. The time intervals between frequency shifts varied from 1 to 50 seconds. See Table 1.

TABLE 1

Role of Time Intervals Between Frequency Changes on the Effectiveness of Electromagnetic Exposure in Modifying ODC Activity Ratio of ODC Activity in Exposed Compared to Unexposed Cells

| | | Time interval between frequency changes (seconds) | | | | |
|---|---|---|---|---|---|---|
| | | 0.1 | 1 | 5 | 10 | 50 |
| (1) | ELF (55 to 65 Hz) | — | 1 | 1.4 | 1.9 | 2.3 |
| (2) | Microwaves (modulated alternately by 65 and 55 Hz) | 1 | 1 | 1.5 | 2.1 | 2.1 |

It can be seen from Table 1, (1), that when the time intervals between frequency shifts in the electromagnetic fields were 10 seconds or greater, the electromagnetic field exposure resulted in a two-fold increase in ODC activity. When the time intervals between frequency shifts (i.e. between 55 Hz and 65 Hz) were shortened to less than 10 seconds, the effectiveness of these ELF (extremely low frequency) fields in increasing ODC activity diminished. At 1 second and below the fields had no effect at all (i.e., the activity of the exposed mammalian cells was the same as for unexposed cells). Thus we see that introducing changes in parameters of the electromagnetic field at short enough time intervals prevents any action of the field on cell function.

This finding applies to electromagnetic frequencies as high as the microwave region. Similar data were obtained using 0.9 GHz microwaves modulated at frequencies changing between 55 and 65 Hz at intervals of time ranging from 0.1 to 50 seconds. A 60 percent amplitude modulation was used and the specific absorption rate was 3 mW/g. As can be seen in Table 1, (2), when the time interval was 10 seconds or greater, this microwave field also caused a two-fold increase in ODC activity. At shorter time intervals the effect of the field on ODC activity diminished. When the time intervals between changes were one second or less, the field had no effect on ODC activity.

To further demonstrate the protective effect of my confusion fields, I studied the effects of modulation on the ability of exogenous electromagnetic fields to act as a teratogen and cause abnormalities in chick embryos. In experimental methods now described, I modulated the amplitude of a 60 Hz electromagnetic field. Fertilized White Leghorn eggs were obtained from Truslow Farms of Chestertown, Md. These were placed between a set of Helmholtz coils inside an incubator kept at 37.5° C. During the first 48 hours of incubation one group of eggs was exposed to a 60 Hz continuous wave (cw) sinusoidal electromagnetic field whose amplitude was 1 µT. Another group was exposed to a 60 Hz cw sinusoidal electromagnetic field whose amplitude was 4 µT. Another group of eggs was exposed to a 60 Hz sinusoidal electromagnetic field whose amplitude was varied from 1.5 to 2.5 µT at 1 second intervals. Control eggs were simply placed in the incubator and not exposed to an electromagnetic field. After 48 hours of incubation the embryos were removed from their shells and examined histologically. It was found that the control group (not exposed to the 60 Hz magnetic field) exhibited about 8 percent abnormalities. The embryo groups exposed to 1 µT and 4 µT fields had a higher abnormality rate (14 percent) than the controls indicating that these fields had indeed induced abnormalities. Those embryos exposed to the fields modulated at 1 second intervals had an abnormality rate the same as the unexposed eggs. Thus the 1 second modulation (or coherence time) effectively eliminated the teratogenic effect of the magnetic field.

BRIEF DESCRIPTION OF THE DRAWINGS

I will next describe various techniques and apparatus for carrying out my invention. These descriptions will be aided by reference to the accompanying drawings, in which:

FIG. 1 is a plot of amplitude vs. time of a sinusoidal function modulated as to amplitude.

FIG. 2 is a plot of amplitude vs. time of a sinusoidal function modulated as to frequency.

FIG. 3 is a diagram of a circuit for modulating electric current through a plumbing pipe.

FIG. 4 is a diagram of a protective circuit for an electric blanket.

DETAILED DESCRIPTION OF PRESENTLY PREFERRED EMBODIMENTS

Figure 5:
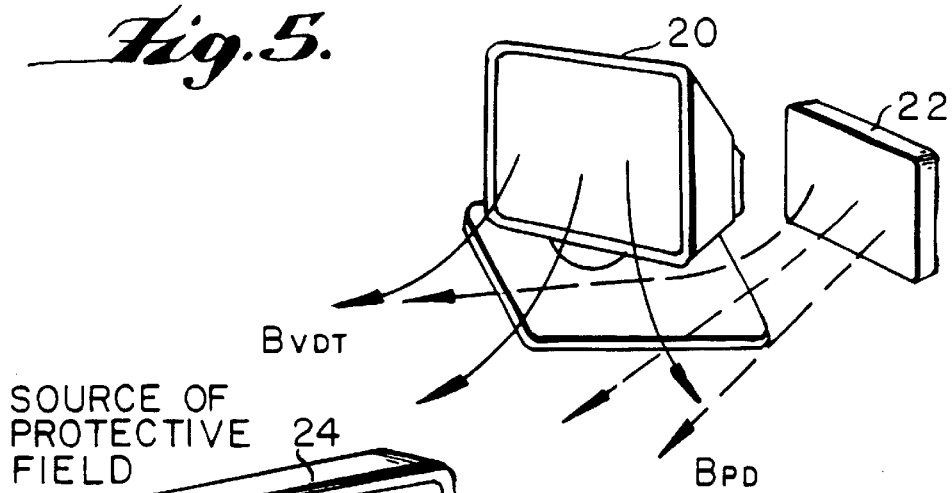
FIG. 5 is a diagram of a protective apparatus for use with a video display terminal.

There are many different methods and related apparatus of converting a harmful field into a "confusion" field. Some of these are as follows:

1. Place several time dependent grounding devices on the metal plumbing pipes. These devices cause fluctuating paths for electric current in the plumbing pipe and therefore fluctuating fields in any room in the house or other human or animal-occupied structure.

2. Insert fluctuating resistance paths in series with heating devices such as electric blankets.

3. Place devices near appliances and computers which create fluctuating electromagnetic fields near the computers or appliances. These fields are superimposed on the uncontrolled source of the original harmful field.

4. Eliminate hazards created by the electromagnetic fields in the region around electric devices, by modulating the electric current flowing in the device. The modulation can be caused by means which are external or internal to the device.

5. Eliminate hazards created by the electromagnetic fields in the region around electric devices, by modulating the voltage in the device. This modulation can be caused by means which are external or internal to the device.

6. Eliminate hazards created by the electromagnetic fields in the region around electric devices, by modulating the electromagnetic field around the device. This modulation can be caused by means which are external or internal to the device.

7. Eliminate hazards created by the electromagnetic fields in the region around electric heaters, such as electric blankets, heating pads, and electrically heated water beds, by modulating the current and/or voltage in the device. This modulation can be caused by means which are external or internal to the device.

8. Eliminate hazards created by the electromagnetic fields in the region around electric power distribution systems by superimposing a modulated electromagnetic field in the region of space to be protected.

9. Eliminate hazards created by the electromagnetic fields in the region around the metallic plumbing used to ground electrical lines by superimposing a modulated electromagnetic field in the region of space to be protected. This can be done by passing modulated currents through the plumbing itself or by passing modulated currents through external circuits.

10. Eliminate hazards created by the electromagnetic fields around cathode ray tube devices such as video display terminals and television sets by superimposing a modulated electromagnetic field. The source of this electromagnetic field can be placed either inside or external to the device.

11. Eliminate hazards created by the electromagnetic fields in the region around microwave ovens by superimposing a modulated electromagnetic field in the region of space to be protected.

12. Clearly many of the above procedures may be adapted to protect laboratories, industrial plants, etc., wherein cells not in humans or in multi-cell living systems may exist.

SPECIFIC PROTECTIVE ARRANGEMENTS

Any voltage, current, electric field, magnetic field, or electromagnetic field which varies repetitively in time can be described by its waveform, peak amplitude (A), frequency (period), direction and phase. Modulation of the wave refers to the time dependent variation of any of these parameters. For example, pulse modulation of the amplitude of any of the parameters refers to a change in amplitude. Two examples of this modulation are shown in FIGS. 1 and 2. In FIG. 1 the amplitude is modulated by a pulse. Thus, for a period of time, $T_1$ the amplitude of the sinusoidally varying voltage is $A_1$. For a second time period, $T_2$, the amplitude is $A_2$. The values of $T_1$ $T_2$ need not be equal but they must each be about second or less for best results. Many variations in the modulation of a time varying voltage can be used, such as a sinusoidal modulation of the original sine wave. Thus, a 60 Hz sine voltage could be amplitude modulated by a 1 Hz sinusoidal variation. Another possibility is a saw tooth variation in the amplitude of a 60 Hz sine voltage. In all of the possible modulated fields, at least one of the parameters, such as amplitude, waveform, phase, direction or frequency must not be constant for a time duration of more than about 1 second.

Thus, for example, in FIGS. 1 and 2 the values of $T_1$ and $T_2$ must not be longer than about 1 second. For best results, $A_1$ should be greater than $1.2A_2$, and preferably greater than $2A_2$. Similarly $w_1$ (omega$_1$) should be at least 20 percent larger than $w_2$ and preferably 50 percent larger than $w_2$.

Whenever a microwave field is being modulated at a frequency of 100,000 Hz or less, steps should be taken to achieve protection under my present invention by periodic parameter changing as described herein.

Protection from copper plumbing may readily be achieved. With reference to FIG. 3, devices 10 are switches either electronically or mechanically controlled which switch on and off at intervals of one second (e.g. one second on and one second off). During the "on" intervals this will cause some of the current flowing past point A and B in the copper pipe 12 to alternately flow through ground rather than entirely through the pipe. Thus, the current flow from A to B (which creates an electromagnetic field in the working and living spaces of the structure) will be modulated (by reduction in current) at intervals of no greater than one second. The number of devices needed will depend on the complexity of the piping.

Protection from electric blankets is readily achieved. In FIG. 4 device 14 (the protective circuit) is a switch which turns the electric current through the blanket 16 on and off at intervals of one second. The device 14 need not switch the current completely off. It could, for example, reduce the current by 50 percent, and then within one second return the current to its full value. The device 18 is the usual thermostat supplied with electric blankets. Neither the "on" nor the "off" interval should be greater than 3 seconds, and preferably one second.

Harmful effects of video display terminals may be avoided. In FIG. 5 the video display terminal 20 is protected by a source 22 of electromagnetic field. $B_{VDT}$ and $B_{PD}$ are, respectively, the magnetic fields of the video display terminal (VDT) and the protective device (PD). The average amplitude of $B_{PD}$ at any point in the region to be protected should be greater than 50 percent of the amplitude of the field due to the VDT. Preferably, the average amplitude $B_{PD}$ should be at least twice the amplitude of $B_{VDT}$. If the protective field of PD is in the same direction as the VDT field it will be most effective. If the PD field is perpendicular to the VDT field, it must be five times larger than the VDT field.

Figure 6:
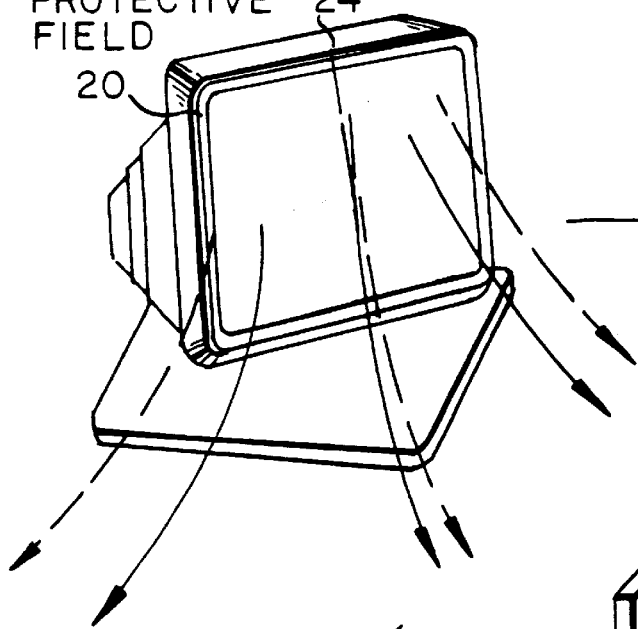
FIG. 6 is a diagram of another form of protective circuit for use with a video display terminal.

FIG. 6 is a system like that in FIG. 5 except here the PD 24 is a coil mounted around the VTD 20.

The protective device can be any device which generates a time varying modulated electromagnetic field.

For example, if a coil with ten turns of wire is to be used, it can be mounted either as in FIG. 1, or in FIG. 2. In FIG. 1 the coil is placed on a surface near the VDT and oriented so that its field intersects the field of the VDT. In FIG. 2 the coil is placed around the outer edge of the front of the VDT. In a typical VDT the coil could be a square about 40 cm on each side. The average current in the coil should be adjusted so that the average field at the front and center of the monitor due to the coil is preferably about equal to that field at the same point due to the VDT. For example, if the average field at the very front of the monitor is 10 $\mu$T a 10 turn coil of wire 40 cm on edge could have a 60 Hz cw current of approximately 0.35 amps flowing through it. The current could be alternatively 0.5 amps for 1 second and then 0.2 amps for 1 second.

It will be understood that a standard TV set (one case of VDT) can be protected in the same manner as VDTs or "computers". Oscilloscopes may similarly be protected.

Figure 7:
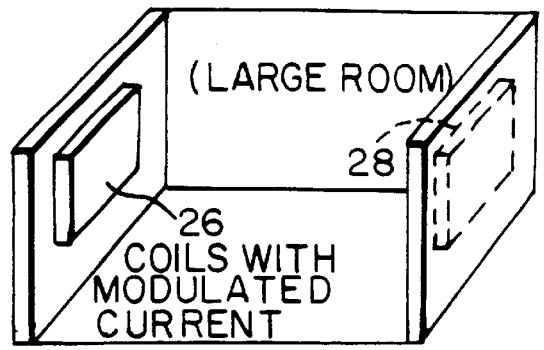
FIG. 7 is a diagram of a protective system for use in a space occupied by humans.

Large areas may also be protected. Referring to FIG. 7, 26 and 28 are large coils of wire (e.g. 7 ft high by 7 ft wide) mounted on or near opposite walls of a room, or on the floor and ceiling. The latter configuration is more effective than the former when the ambient fields are in a vertical direction. It is assumed that the room is exposed to a cw electromagnetic field that is dangerous to living systems. Modulated current (e.g., "on" and "off" at one second intervals) flows through the coils. The current and the modulation in coil 26 is kept in phase with the current and modulation in coil 28. The pair of coils act as Helmoholtz coils and tend to keep the field in the protected region more uniform than if a single coil were used. The average amplitude of the current in the coils should be such that the electromagnetic field produced by the coils at every point in the region to be protected is at least 50 percent of the erstwhile ambient field and preferably 5 to 10 times the ambient value.

A single coil can be used instead of the a pair of coils. The larger the coil the better; a larger coil will provide a more uniform protected region than a small one.

Figure 8:
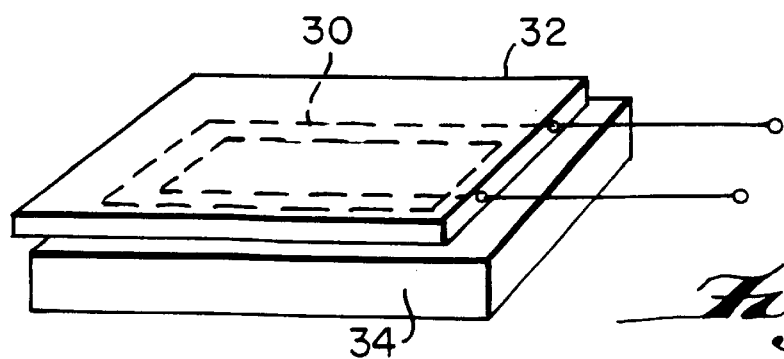
FIG. 8 is a diagram of a mat for placement on or under a mattress used for sleeping purposes.

Special mats containing coils can be used in the home, laboratory, or other living system inhabited place to provide general protection. For example, a large percentage of the time spent at home is by a human sleeping on a bed. Thus, it would be useful for those who live near power distribution lines to use a device which puts the human in a protective "confusion" field during the time during which he is lying on the bed. As shown in FIG. 8, this can be done by imbedding a many turn coil of wire 30 in a mat 32 and placing this mat either on or under the mattress 34, but near the head of the bed for maximum protection of the vital organs. The wire should be of low resistance, since it would be used year round and should not have significant heating of the bed or its occupants. This coil of wire would have the modulated current flowing through it during all seasons. The modulated electromagnetic field would protect the occupants of the bed from the ambient electromagnetic fields in the room. For example for a queen size bed a square coil of wire with 10 turns approximately 60 inches by 60 inches square and with 0.14 amperes of current flowing will yield at the center of the coil a magnetic field in the vertical direction of about 1 micro Tesla. If the bed is over 100 feet away from a power line 20 feet in the air, the ambient magnetic field due to the power line is also in the vertical direction. Thus, we have an optimum alignment of the field of the coil and that of the power line. To create a confusion field the current in the coil should vary from about 0.03 amperes to 0.07 amperes and back at least once every second yielding a coil field at the center which fluctuates between 0.5 and 0.2 $\mu$T. Assuming that the power line is 1 $\mu$T, the total field near the center will (if the coil field is in phase with the power line field) change from 1.2 $\mu$T to 1.5 $\mu$T and back every second. If the fields are out of phase the net field will vary from 0.5 to 0.75 $\mu$T every second. Either of these conditions would protect the occupants from exposure to the power line field. The above coil could be combined within an electric blanket so that the blanket would serve a dual purpose of heating and protecting.

Such mats also may be adapted for use with chairs, or placed on tables or kitchen counters, or wherever humans or animals spend considerable time.

Conclusion

Upon reading this application many variations and modifications of my method and apparatus inventions will become apparent to the reader. Therefore, the scope of my inventions is to be determined from the appended claims.

I claim:

1. A method of inhibiting the adverse effect on a living system of an ambient time varying field having as characteristic parameters one or more of amplitude, period, phase, waveform and direction, the field having an electric component and a magnetic component, which method comprises the step of changing at least one of the characteristic parameters of said field to which the living system is exposed, and the step of effecting the change within time intervals of less than 10 seconds.

2. A method of inhibiting the adverse effect on a living system of an ambient time varying field having as characteristic parameters one or more of amplitude, period, phase, waveform and direction, the field having an electric component, which method comprises the step of changing at least one of the characteristic parameters of said field to which the living system is exposed, and the step of effecting the change within time intervals of less than ten seconds.

3. A method of inhibiting the adverse effect on a living system of an ambient time varying field having as characteristic parameters one or more of amplitude, period, phase, waveform and direction, the field having a magnetic component, which method comprises the step of changing at least one of the characteristic parameters of said field to which the living system is exposed, and the step of effecting the change within time intervals of less than ten seconds.

4. A method as in any of one of claims 1, 2 or 3 in which the parameter of said field which is changed is the amplitude of the field.

5. A method as in any of one of claims 1, 2 or 3 in which the parameter of said field which is changed is the period of the field.

6. A method as in any of one of claims 1, 2 or 3 in which the parameter of said field which is changed is the phase of said field.

7. A method as in any of one of claims 1, 2 or 3 in which the parameter of said field which is changed is the waveform of said field.

8. A method as in any of one of claims 1, 2 or 3 in which the parameter of said field which is changed is the direction of said field in space.

9. A method as in any of one of claims 1, 2 or 3 in which each parameter change in said field occurs at irregular time intervals, with the longest time intervals between changes being less than approximately 10 seconds.

10. A method as in claim 4 in which each parameter change in said field occurs at irregular time intervals, with the longest time intervals between changes being less than approximately 10 seconds.

11. A method as in claim 5 in which each parameter change in said field occurs at irregular time intervals, with the longest time intervals between changes being less than approximately 10 seconds.

12. A method as in claim 6 in which each parameter change in said field occurs at irregular time intervals, with the longest time intervals between changes being less than approximately 10 seconds.

13. A method as in claim 7 in which each parameter change in said field occurs at irregular time intervals, with the longest time intervals between changes being less than approximately 10 seconds.

14. A method as in claim 8 in which each parameter change in said field occurs at irregular time intervals, with the longest time intervals between changes being less than approximately 10 seconds.

15. A method as in any of one of claims 1, 2 or 3 in which each parameter change in said field occurs at regular time intervals, with each time interval between changes being less than approximately 10 seconds.

16. A method as in claim 4 in which each parameter change in said field occurs at regular time intervals, with each time interval between changes being less than approximately 10 seconds.

17. A method as in claim 5 in which each parameter change in said field occurs at regular time intervals, with each time interval between changes being less than approximately 10 seconds.

18. A method as in claim 6 in which each parameter change in said field occurs at regular time intervals, with each time interval between changes being less than approximately 10 seconds.

19. A method as in claim 7 in which each parameter change in said field occurs at regular time intervals, with each time interval between changes being less than approximately 10 seconds.

20. A method as in claim 8 in which each parameter change in said field occurs at regular time intervals, with each time interval between changes being less than approximately 10 seconds.

21. A method as in any of one of claims 1, 2 or 3 in which said ambient field is at least in part the result of a time varying electric current flowing in a conductor.

22. A method as in any of one of claims 1, 2 or 3 in which the change in said ambient field is accomplished by effecting a change in at least one source of the ambient field.

23. A method as in any of one of claims 1, 2 or 3 in which the change in said ambient field is accomplished by superimposing upon said ambient field one or more fields caused by one or more additional sources.

24. A method as in any of one of claims 1, 2 or 3 in which said ambient field is one resulting from signals below AM band radio frequencies.

25. A method as in any of one of claims 1, 2 or 3 in which said ambient field is one resulting from signals in AM band radio frequencies or higher frequencies.

26. A method as in claim 24 in which said signals are modulated with signals of lower frequencies.

27. A method as in claim 25 in which said signals are modulated with signals of lower frequencies.

28. A method as in claim 27 in which the ambient field results from microwave frequency signals and the modulation frequency is less than 100,000 Hz.

29. A method as in claim 9 in which the time interval between changes is approximately one second or less.

30. A method as in claim 10 in which the time interval between changes is approximately one second or less.

31. A method as in claim 11 in which the time interval between changes is approximately one second or less.

32. A method as in claim 12 in which the time interval between changes is approximately one second or less.

33. A method as in claim 13 in which the time interval between changes is approximately one second or less.

34. A method as in claim 14 in which the time interval between changes is approximately one second or less.

35. A method as in claim 15 in which the time interval between changes is approximately one second or less.

36. A method as in claim 16 in which the time interval between changes is approximately one second or less.

37. A method as in claim 17 in which the time interval between changes is approximately one second or less.

38. A method as in claim 18 in which the time interval between changes is approximately one second or less.

39. A method as in claim 19 in which the time interval between changes is approximately one second or less.

40. A method as in claim 20 in which the time interval between changes is approximately one second or less.

41. Apparatus for inhibiting the adverse effect on a living system of an ambient time varying field having as characteristic parameters one or more of amplitude, period, phase, waveform and direction, the field having an electric component and a magnetic component, which apparatus comprises a means for changing at least one of the characteristic parameters of said field to which the living system is exposed, and a means for effecting the change within time intervals of approximately 10 seconds or less.

42. Apparatus for inhibiting the adverse effect on a living system of an ambient time varying field having as characteristic parameters one or more of amplitude, period, phase, waveform and direction, the field having an electric component, which apparatus comprises a means for changing at least one of the characteristic parameters of said field to which the living system is exposed, and a means for effecting the change within time intervals of approximately ten seconds or less.

43. Apparatus for inhibiting the adverse effect on a living system of an ambient time varying field having as characteristic parameters one or more of amplitude, period, phase, waveform and direction, the field having a magnetic component, which apparatus comprises a means for changing at least one of the characteristic parameters of said field to which the living system is exposed, and a means for effecting the change within time intervals of approximately ten seconds or less.

44. An apparatus as in any one of claims 41, 42, or 43 in which the parameter of said field which is changed is the amplitude of the field.

45. An apparatus as in any one of claims 41, 42, or 43 in which the parameter of said field which is changed is the period of the field.

46. An apparatus as in any one of claims 41, 42, or 43 in which the parameter of said field which is changed is the phase of said field.

47. An apparatus as in any one of claims 41, 42, or 43 which the parameter of said field which is changed is the waveform of said field.

48. An apparatus as in any one of claims 41, 42, or 43 in which the parameter of said field which is changed is the direction of said field in space.

49. An apparatus as in any one of claims 41, 42, or 43 in which each parameter change in said field occurs at irregular time intervals, with the longest time intervals between changes being less than approximately 10 seconds.

50. Apparatus as in claim 44 in which each parameter change in said field occurs at irregular time intervals, with the longest time intervals between changes being less than approximately 10 seconds.

51. Apparatus as in claim 45 in which each parameter change in said field occurs at irregular time intervals, with the longest time intervals between changes being less than approximately 10 seconds.

52. Apparatus as in claim 46 in which each parameter change in said field occurs at irregular time intervals, with the longest time intervals between changes being less than approximately 10 seconds.

53. Apparatus as in claim 47 in which each parameter change in said field occurs at irregular time intervals, with the longest time intervals between changes being less than approximately 10 seconds.

54. Apparatus as in claim 48 in which each parameter change in said field occurs at irregular time intervals, with the longest time intervals between changes being less than approximately 10 seconds.

55. An apparatus as in any one of claims 41, 42, or 43 which each parameter change in said field occurs at regular time intervals, with each time interval between changes being less than approximately 10 seconds.

56. Apparatus as in claim 44 in which each parameter change in said field occurs at regular time intervals, with each time interval between changes being less than approximately 10 seconds.

57. Apparatus as in claim 45 in which each parameter change in said field occurs at regular time intervals, with each time interval between changes being less than approximately 10 seconds.

58. Apparatus as in claim 46 in which each parameter change in said field occurs at regular time intervals, with each time interval between changes being less than approximately 10 seconds.

59. Apparatus as in claim 47 in which each parameter change in said field occurs at regular time intervals, with each time interval between changes being less than approximately 10 seconds.

60. Apparatus as in claim 48 in which each parameter change in said field occurs at regular time intervals, with each time interval between changes being less than approximately 10 seconds.

61. An apparatus as in any one of claims 41, 42, or 43 in which said ambient field is at least in part the result of a time varying electric current flowing in a conductor.

62. An apparatus as in any one of claims 41, 42, or 43 in which the change in said ambient field is accomplished by effecting a change in at least one source of the ambient field.

63. An apparatus as in any one of claims 41, 42, or 43 in which the change in said ambient field is accomplished by superimposing upon said ambient field one or more fields caused by one or more additional sources.

64. An apparatus as in any one of claims 41, 42, or 43 in which said ambient field is one resulting from signals below Am band radio frequencies.

65. An apparatus as in any one of claims 41, 42, or 43 in which said ambient field is one resulting from signals in AM band radio frequencies or higher frequencies.

66. Apparatus as in claim 64 in which said signals are modulated with signals of lower frequencies.

67. Apparatus as in claim 65 in which said signals are modulated with signals of lower frequencies.

68. Apparatus as in claim 67 in which the ambient field results from microwave frequency signals and the modulation frequency is less than 100,000 Hz.

69. An apparatus as in claim 49 in which the time interval between changes is approximately one second or less.

70. An apparatus as in claim 50 in which the time interval between changes is approximately one second or less.

71. An apparatus as in claim 51 in which the time interval between changes is approximately one second or less.

72. An apparatus as in claim 52 in which the time interval between changes is approximately one second or less.

73. An apparatus as in claim 53 in which the time interval between changes is approximately one second or less.

74. An apparatus as in claim 54 in which the time interval between changes is approximately one second or less.

75. An apparatus as in claim 55 in which the time interval between changes is approximately one second or less.

76. An apparatus as in claim 56 in which the time interval between changes is approximately one second or less.

77. An apparatus as in claim 57 in which the time interval between changes is approximately one second or less.

78. An apparatus as in claim 58 in which the time interval between changes is approximately one second or less.

79. An apparatus as in claim 59 in which the time interval between changes is approximately one second or less.

80. An apparatus as in claim 60 in which the time interval between changes is approximately one second or less.

\* \* \* \* \*